United States Patent [19]

Velenyi et al.

[11] 4,283,583
[45] Aug. 11, 1981

[54] ALKYLATION OF AROMATIC HYDROCARBONS IN THE PRESENCE OF COATED ZEOLITE CATALYSTS

[75] Inventors: Louis J. Velenyi, Lyndhurst; Serge R. Dolhyj, Parma, both of Ohio

[73] Assignee: The Standard Oil Company, Cleveland, Ohio

[21] Appl. No.: 53,458

[22] Filed: Jun. 29, 1979

[51] Int. Cl.³ .............................................. C07C 2/68
[52] U.S. Cl. ............................... 585/467; 252/477 R
[58] Field of Search ....................... 585/467; 423/328; 252/477 Q, 477 R

[56] References Cited

U.S. PATENT DOCUMENTS

| 3,251,897 | 5/1966 | Wise | 585/467 |
| 3,730,910 | 5/1973 | Albers et al. | 423/328 |

*Primary Examiner*—Curtis R. Davis
*Attorney, Agent, or Firm*—William D. Mooney; Herbert D. Knudsen; Larry W. Evans

[57] ABSTRACT

Aromatic hydrocarbons, e.g., benzene and analogs thereof, are converted by alkylation to the corresponding alkyl aromatics by contacting the mononuclear aromatic hydrocarbon with an alkylating agent in the presence of a coated zeolite catalyst. This coated catalyst consists of an essentially inert base support having a strongly adherent outer coating containing an active catalytic zeolite material.

26 Claims, 2 Drawing Figures

ALKYLATION OF AROMATIC HYDROCARBONS IN THE PRESENCE OF COATED ZEOLITE CATALYSTS

BACKGROUND OF THE INVENTION

Alkylation of aromatic hydrocarbon compounds employing an aluminosilicate zeolite catalyst is known in the art. For instance, U.S. Pat. No. 3,251,897 describes liquid phase alkylation in the presence of aluminosilicates such as faujasite, heulandite, clinoptilolite, mordenite, dachiardite, zeolite X and zeolite Y. Furthermore, U.S. Pat. No. 2,904,607 shows the alkylation of hydrocarbon compounds in the presence of metallic aluminosilicates, e.g., magnesium aluminosilicate. Finally, U.S. Pat. No. 3,751,506 describes a process for the alkylation of aromatic hydrocarbons comprising contacting these hydrocarbons with an alkylating agent in the vapor phase in the presence of a catalyst comprising a crystalline aluminosilicate zeolite.

Unfortunately, while the prior art aluminosilicate catalysts proposed for the alkylation of benzene provide satisfactory yields of desirable products, they have several disadvantages. First, the use of these prior art catalysts in an alkylation reaction results in a large exotherm. Second, substantial amounts of cracking and rearrangement products are formed. Third, multi-substitution is a problem in these prior art processes. Finally, the activity per gram of active catalytic component is very low. Each of these problems is either eliminated or greatly reduced by the use of the instant coated catalyst. Furthermore, since the coated catalyst contains less of the expensive active catalytic material than prior art catalysts, coated catalysts are less expensive per catalyst charge. Thus, the coated catalysts of the invention provide several advantages in the process for alkylating aromatic hydrocarbons which were heretofore lacking in the art.

SUMMARY OF THE INVENTION

This invention provides an improvement in the process wherein alkyl aromatics are produced by contacting a mononuclear aromatic hydrocarbon with an alkylating agent in the presence of a zeolite catalyst, the improvement comprising using as at least part of the catalyst a coated catalyst having:
 (a) an at least partially porous base support of at least about 20 microns in diameter, said support having an outer surface, and
 (b) a coating substantially on said outer surface, said coating consisting essentially of an active catalytic material containing a zeolite, said coating strongly adhering to said outer surface of said base support.

In a specific embodiment, the present invention provides a process for producing ethylbenzene and/or cumene by contacting benzene with at least one of ethylene and propylene in the presence of a coated zeolite catalyst.

In accordance with this invention, it has been found that alkyl aromatics can be produced in high yields and selectivities by the alkylation of an aromatic hydrocarbon in the presence of a catalyst containing only a small amount of an active catalytic zeolite. Furthermore, this invention provides a process wherein undesired side products produced by cracking, rearrangement and multi-substitution are greatly reduced. Finally, by employing coated catalysts in this alkylation process, the reaction exotherm can be greatly reduced.

DESCRIPTION OF THE DRAWING

The catalysts of the invention are illustrated in the Figures.

DETAILED DESCRIPTION

Figure 1:
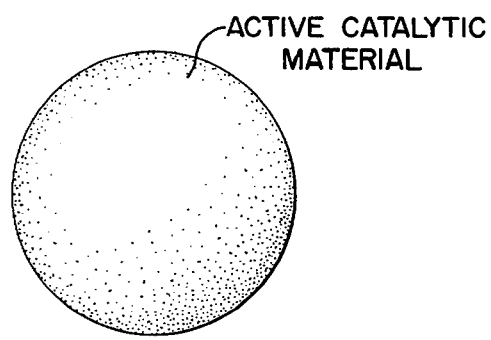
FIG. 1 shows a view of the catalyst of the present invention. The illustrated catalyst is a sphere with the entire outer surface of the sphere being the active catalytic material.
Figure 2:
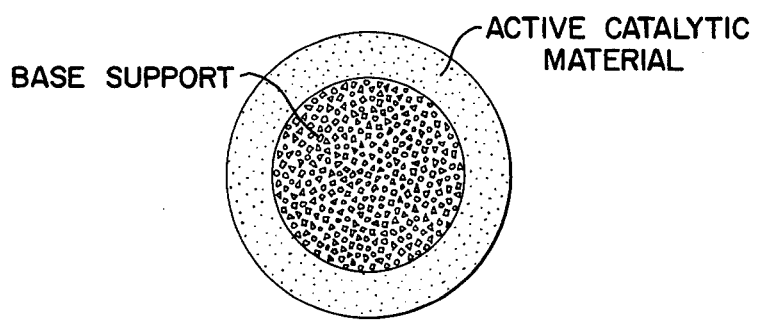
FIG. 2 shows a cross-sectional view of the spherical catalyst of FIG. 1 obtained by cutting the spherical catalyst in half. The catalyst consists of an inner core or base support and an outer coating of an active catalytic material. As can be readily seen from FIG. 2, the active catalytic material is distributed on the outside of the base support and is not distributed uniformly throughout the catalyst.

As noted in the Background of the Invention above, the alkylation of aromatic hydrocarbons is a well known process. The present invention relates to the use of a coated zeolite catalyst in this known reaction.

Reactants

The inventive alkylation reaction is accomplished by contacting an aromatic hydrocarbon with an alkylating agent in the presence of a coated zeolite catalyst. This invention finds wide applicability in the alkylation of all types of aromatic hydrocarbons.

Aromatic hydrocarbons containing 5 to 7 carbon atoms in the ring are preferred in this process. These aromatic compounds can be substituted with $C_{1-12}$ alkyls, $C_{6-12}$ cycloalkyls, and $C_{6-12}$ aryls. Especially preferred reactants include benzene and substituted benzene substituted with one to five $C_{1-4}$ alkyls. Specific examples of aromatic compounds which are useful in the process of this invention include benzene, ethylbenzene, cumene (isopropyl benzene), toluene, xylene, and durene (tetramethylbenzene).

The alkylating agents useful in this process include $C_{2-10}$ alkenes, $C_{1-10}$ alkyl halides, $C_{1-10}$ aldehydes, $C_{5-12}$ cyclic olefins and $C_{1-10}$ alcohols. Preferred alkylating agents are $C_{2-4}$ alkenes.

This reaction is preferably carried out while maintaining an overall aromatic hydrocarbon to alkylating agent mole ratio of about 1:1 to 20:1, more preferably about 2.5:1 to 10:1. If desired, a carrier gas and/or a solvent which are inert to the reactants, products and catalyst can be included in the reaction system.

Process Conditions

This process can be accomplished both in a batch mode and continuously with both fixed and fluid catalyst beds. The instant reaction can also take place in either the gas phase or liquid phase.

Operating conditions employed in this process will be dependent, at least in part, on the specific alkylation reaction being affected. Moreover, such factors as temperature, pressure, presence of diluent, and the molar ratio of the reactants will have important effects on the process.

The reaction is normally carried out in a single stage operation, i.e., all of the reactants and the catalyst necessary for the reaction are brought together at the same time and not in stepped additions. However, the reaction can be carried out in stages if desired.

The reaction temperature is normally maintained between room temperature and 400° C., preferably 100°–300° C., and more preferably 150°–250° C. The reaction pressure is normally maintained at atmospheric pressure but sub-atmospheric and super-atmospheric pressure can also be used. When the reaction is carried out in the batch mode, the reactants and catalyst are contacted with one another for a period of 10 minutes to six hours, preferably more than one-half to three hours. A reaction time of less than ten minutes or more than six hours can be used if desired although better results will be obtained if the reaction time is maintained within this range. If the process is carried out in a continuous basis in a fixed bed system, the apparent contact time of the catalyst and the reactants may vary from about 0.1 to 20 seconds, preferably 1–10 seconds and more preferably about 3 seconds. Normally, a longer contact time is used for fluid-bed processes. In general, lower reaction temperatures require longer contact times and higher reaction temperatures require shorter contact times.

Catalyst

The coated catalyst of this invention can be obtained by the method shown in U.S. Pat. No. 4,077,912, which is herein incorporated by reference. Broadly, this method involves partially wetting the base support material with a liquid. The base support is then allowed to dry until the outside surface of the support is dry to the touch. The prewetted support is then contacted with a powder of the catalytically active material and the mixture is gently agitated till the catalyst is formed. If the outside surface of the catalyst is wet, then the active catalytic material will agglomerate into separate aggregates when coating of the support is attempted.

The gentle agitation is most conveniently conducted by placing the partially wet support on a rotating drum and adding the active catalytic material until none is taken up by the support. This can be very economically done.

The liquid used to wet the support may include inorganic or organic liquids e.g., water, acids and salt solutions, and is essentially dependent upon the type of active catalytic material employed. The liquid and the active catalytic material must have a high degree of attraction for each other. For example, if a hydrophilic active catalytic material is used, water could be used to wet the support. On the other hand, if the hydrophobic catalytic material is used, either organic solvents such as petroleum, ethers and alcohols or inorganic support materials such as alumina or aluminum nitrate could be used. Water and alcohol are the preferred liquids.

More specifically, the catalyst of this invention is prepared by:

(a) contacting a base support of at least about 20 microns in diameter with an excess of liquid in such a manner that the liquid is absorbed by the support to produce a wet support;

(b) drying said wet support to provide a partially wet support, which partially wet support is defined as one that does not have the appearance of a liquid on the outer surface of the support, but has at least some liquid absorbed into the support;

(c) contacting the partially wet support with a powder of an active catalytic material; and (d) gently agitating the mixture of the partially wet support and active catalytic material to produce the catalyst.

It can readily be seen that the first two steps can be combined by the addition of a measured amount of liquid that would give a partially wet support. Thus, there would be no need for the intermediate drying step.

As noted above, the catalyst of the present invention contains two discreet parts—a base support and an active catalytic material.

The base support can be selected from a wide choice of support materials known in the art. This material must have a diameter of at least about 20 microns. Preferably, the base support has a diameter of about 0.5 millimeters to about 10 millimeters, but there is no limitation on the maximum size of the base support material.

The base support material must be at least partially porous. By this is meant that the support material must be susceptible to the penetration of a liquid. The preferred base support materials are capable of absorbing at least about 5% by weight of water based upon the weight of the support.

The base support materials used in the present invention are well known in the art and are either commercially available or can be conveniently prepared. For example, U.S. Pat. No. 3,145,183 (herein incorporated by reference) shows the preparation of support balls that are useful in the preparation of the catalyst of this invention. Also, base support materials could be prepared by compacting a suitable support material into the desired shape.

Although the attached drawing shows a spherical shaped base support, the instant base support can be of any shape. Preferably, the base support has a spherical shape in order to minimize the pressure drop in the reactor.

Even though any support material can be used as the base support in the present invention, certain support materials are preferred. In this regard, a preferred base support comprises an essentially inert, low surface area material. Preferred are those support materials that have surface areas of less than about 20 square meters per gram. Especially preferred base supports have surface areas of less than 5 square meters per gram.

The preferred base support materials include silica, alumina, alumina-silicate, silicon carbide, titania, and zirconia. Especially preferred among these supports are silica, alumina and alumina-silicate.

A second component of the catalyst of the present invention comprises an active catalytic material. This active catalytic material can comprise either one or more zeolites or a mixture of one or more zeolites and a coating support material. The active catalytic material can be about 0.5% to 95% by weight of the catalyst particle. Preferably, it is 5% to 30% by weight of the catalyst particle.

The active catalytic zeolites used in this invention can comprise any type of zeolite. These zeolites are not novel and their preparations are described in the prior art. For example, U.S. Pat. No. 3,251,897 discloses catalysts comprising mordenite, faujasite, X-type zeolites and Y-type zeolites; and U.S. Pat. No. 3,751,506 shows catalysts comprising crystalline aluminosilicate zeolites. These patents are herein incorporated by reference. X-type and Y-type zeolites are described in detail in both Chapters 18–20 of Meler and Uytterhoeven, "Molecular Sieves," *American Chemical Society*, Washington D.C., (Copyright 1973) and in U.S. Pat. No. 3,130,007, which are also herein incorporated by reference.

The preferred catalytic zeolites comprise either Y-type zeolites or zeolites with a sodium or alkali metal content of less than 1% by weight. In one embodiment, the Y-type zeolite employed is Linde's SK-500, which is a well known commercially available catalyst support. Linde's SK-500 is composed of 65.0 weight persent $SiO_2$, 22.7 weight percent $Al_2O_3$, 1.6 weight percent $Na_2O$ and 10.7 weight percent various rare earth metals. Rare earth exchanged Y-type zeolites other than Linde's Sk-500 can be employed in the present invention, the specific rare earth impregnating the Y-type zeolite being unimportant. In this connection, since it is expensive to separate one rare earth from another, commercially available rare earth-exchanged Y-type zeolites are made with mixtures of different rare earths rather than a single rare earth.

In an alternate embodiment, the zeolite employed is Linde's LZ-Y82. This zeolite, comprising 65.5 weight % $SiO_2$, 33.6% $Al_2O_3$, 0.15% $Na_2O$, 0.18% $Fe_2O_3$ and 0.03% CaO, is also commercially available.

The coating support material can also be selected from a wide choice of support materials known in the art. The coating support material can be the same as or different from the base support material. In fact, any support material which is stable under the reaction conditions is within the scope of the instant invention.

Preferably the coating support material is a high surface area material and has a surface area of greater than 20 square meters per gram. Most preferably the surface area is greater than 100 square meters per gram.

The coated catalyst may be employed as 100% of the total reactor charged. In an alternate embodiment, the coated catalyst may be used in conjunction with a conventional alkylation catalyst, in which case the amount of coated catalyst would be some fraction of the total reactor charged. The coated catalyst can be either intimately mixed with the conventional catalyst or employed as a separate layer within the reactor.

Recovery

The reaction product obtained upon completion of this reaction is normally in the form of a liquid and composed primarily of unreacted reactants and products. The reaction products can be subjected to suitable known separation techniques to yield the desired end products, namely the alkyl aromatic.

For example, the liquid reaction products can be separated into component parts by the use of an acetone trap. Further separation can be accomplished by distillation or any other suitable separation technique.

The alkyl aromatic products have many uses. For example, they may be used as chemical intermediates or as solvents. In particular, ethyl benzene is used in large quantities for the manufacture of styrene monomer which is the raw material for polystyrene, a plastic product in great demand. Cumene is used both in preparation of phenol and as a blending agent for fuels.

SPECIFIC EMBODIMENTS

In order to more thoroughly describe the present invention, the following working examples are presented. In these examples yield is defined as:

$$Yield = \frac{\text{moles carbon in reactant converted to product}}{\text{moles carbon in reactant fed}} \times 100$$

Also, P means productivity and is defined as:

$$P = \frac{\text{grams carbon in product}}{\text{grams of active catalytic zeolite/hr.}}$$

The productivity values relate to the effectiveness of the active sites, ultimately at the atomic levels. In this regard, the higher the productivity value, the higher the performance of the catalyst per gram of active catalytic zeolite. This becomes a very important factor when expensive zeolite catalysts are used.

All of the following comparisons and working Examples relate to the production of cumene from benzene. In Comparisons A, B and C this reaction is conducted in the presence of an Sk-500 (uncoated) catalyst at various different temperatures. In Comparisons D, E and F this reaction is conducted in the presence of LZ-Y 82 (uncoated) catalyst particles at various reaction temperatures. In working Examples 1 and 2 the above reaction is conducted in the presence of a coated catalyst comprising 5% Sk-500 and 95% Alundum at various temperatures. Similarly, working Examples 3, 4 and 5 use a coated catalyst comprising 10% SK-500 and 90% Alundum. Finally, in working Examples 6, 7 and 8, the above reaction is conducted in the presence of a coated catalyst comprising 10% LZ-Y82 at various reaction temperatures. The experiments were conducted as follows:

Comparison A

An active catalytic zeolite, Linde's SK-500, was purchased from Union Carbide Corporation. This catalyst was used in the uncoated form to convert benzene to cumene by the following procedure.

A 20 cc fixed-bed reactor was packed with 17.5 cc of the above catalyst (10/30 mesh). 2.5 cc of Alundum were placed on top of the catalyst material. The Alundum served as the vaporizer for the liquid feed. The catalyst was activated before use in the presence of air at 230° C. for 1 hr. The temperature was then raised to 550° C. and kept at this temperature for 2 hrs. The air was turned off and the catalyst was cooled to the desired reaction temperature under nitrogen.

The liquid feed, benzene, was pumped directly into the catalyst bed. The gaseous feed, propylene and nitrogen, were introduced via a calibrated rotometer. A benzene/propylene/$N_2$ molar ratio of 5/1/5, a contact time of about 3 seconds and 1 atmosphere pressure were adopted for these experimental runs. The temperature was varied for each run as shown in Table 1.

The products were collected and analyzed. The results are shown in Table 1.

Comparisons D, E and F

An active catalytic material containing 80% LZ-Y 82 and 20% $SiO_2$ was prepared as follows. 72 grams of LZ-Y 82 powder was purchased from Union Carbide Corporation. This zeolite material was placed in a 1-liter beaker with 250 cc of distilled water. After being stirred for a few minutes, 18 grams of colloidal $SiO_2$ (Nalco 41 DO1) were added and the mixture was heated with continuous stirring. The $SiO_2$ acted as a binder and was used so that 10/30 mesh catalyst particles could be formed. The water was then evaporated from this mixture until a thick white paste was formed. This paste was dried overnight at 110° C.

The catalyst was then charged to the apparatus described in Comparison A under substantially the same conditions. The results are shown in Table 1.

EXAMPLES 1 and 2

The powdered active catalytic material of Comparison A was coated on Alundum particles sold by the Norton Chemical Co. bearing the trade designation SA 52 09 as outlined below. 38 grams of the 10/30 mesh Alundum balls were sprayed with 3.04 grams of water and then rolled for about 10 minutes until the surface of the Alundum particles appeared dry. These particles were then rolled in 0.4 grams of the active catalytic material, Sk-500, for about 10 minutes. This step was repeated sequentially four more times until a total of 2 grams of active catalytic material had been coated on the Alundum particles. The rolling of the support was done on a glass jar rotated at a slightly inclined angle form horizontal. This rotating action provided sufficient agitation so that the active catalytic material formed a substantially uniform coating on the Alundum support. The active catalytic material did not permeate the support. The catalyst was then dried overnight at 110° C.

The catalyst obtained by the above procedure contained 5% active catalytic material and 95% Alundum support by the weight. The catalyst was charged to the apparatus described in Comparison A under substantially the same conditions. The results are shown in Table 1.

EXAMPLES 3–5

The basic procedure of Examples 1 and 2 was repeated to obtain a coated catalyst comprising 10% SK-500 and 90% Alundum. The procedures were identical accept that 45 grams of Alundum, 3.8 grams of water and a total of 5 grams of SK-500 were used. The results are shown in Table 1.

EXAMPLES 6–8

The active catalytic material obtained in Comparison D was coated on Alundum particles sold by the Norton Chemical Co. under their trade designation SA 5223 as outlined below. 61.25 grams of 10/30 mesh Alundum particles were sprayed with 5.32 grams of water and then rolled for 10 minutes until the surface of the Alundum particles appeared dry. The Alundum particles were then rolled in 1.7 grams of the active catalytic material for about 10 minutes. This step was repeated sequentially four more times until a total of 8.75 grams of active catalytic material had been coated on the Alundum particles. The rolling of the support was done in a glass jar rotated at a slightly inclined angle from horizontal. This rotating action provided sufficient agiation so that the active catalytic material formed a substantially uniform coating on the Alundum support. The active catalytic material did not permeate the support. The catalyst was then dried over the weekend at 110° C.

The catalyst obtained by the above procedure contained 10% LZ-Y82, 2.5% $SiO_2$ and 87.5% Alundum by weight. This catalyst was charged to the apparatus described in Comparison A under substantially the same conditions. The results are shown in Table 1

Table 1 shows that a substantial improvement in performance per gram of active catalytic zeolite is realized using the coated catalyst of the instant invention. In fact, the active catalytic zeolite can be up to 12 times more productive when in the coated form rather than in the uncoated form. Since many of these active catalytic zeolites are very expensive, any increase in their productivity has great commercial import. Also, Table 1 shows that the severe exotherm of this reaction can be greatly reduced by the use of coated catalysts.

Finally, a further unexpected advantage is obtained by the use of the coated catalyst. In this regard, Table 1 shows that the yield of the undesired cracked and rearranged products is almost totally eliminated by the use of the inventive coated catalyst. Thus, the separation of these undesired products from the desired product is no longer necessary.

Although only a few embodiments of the present invention have been specifically described above, it should be appreciated that many additions and modifications can be made without departure from the spirit and scope of the invention. These and all other modifications are intended to be included within the scope of the present invention, which is to be limited only by the following claims.

TABLE I

ALKYLATION OF BENZENE

Feed: Benzene/Propylene/$N_2$-5/1/5
Contact Time: ~ 3 Seconds
Pressure: 1 Atmosphere

| Example | Catalyst | Temp. (°C.) | Exotherm (°C.) | Catalytic Material (gms) | Selec. (%) Cumene | Yield (%) Cracked & Rearranged Products* | Productivity (P) | Relative Prod. (PR) | $= \frac{P \text{ Coated}}{P \text{ Uncoated}}$ |
|---|---|---|---|---|---|---|---|---|---|
| Comparison A | SK-500 | 248 | 11 | 10.98 | 74.6 | 10.23 | 2.18 | 0.2896 | 1.000 |
| Comparison B | " | 302 | 8 | 10.98 | 57.6 | 8.44 | 4.92 | 0.2336 | 1.000 |
| Comparison C | " | 351 | 7 | 10.98 | 46.3 | 5.59 | 6.47 | 0.1429 | 1.000 |
| Comparison D | 80% LZ-Y82 20% $SiO_2$ (uncoated) | 251 | 17 | 6.4 | 63.1 | 8.82 | 4.45 | 0.4233 | 1.000 |
| Comparison E | 80% LZ-Y82 20% $SiO_2$ (uncoated) | 302 | 4 | 6.40 | 77.2 | 15.55 | 0.98 | 0.7019 | 1.000 |
| Comparison F | 80% LZ-Y82 20% $SiO_2$ (uncoated) | 350 | 7 | 6.40 | 70.9 | 7.40 | 2.47 | 0.3805 | 1.000 |
| 1 | 5% SK-500 95% Alundum (coated) | 249 | 1 | 0.82 | 61.0 | 2.14 | 0 | 0.6757 | 2.333 |
| 2 | 5% SK-500 95% Alundum (coated) | 301 | 0 | 0.82 | 69.9 | 2.25 | 0 | 0.8276 | 3.543 |
| 3 | 10% SK-500 90% Alundum | 250 | 0 | 1.61 | 49.0 | 2.60 | 0 | 0.4236 | 1.463 |

TABLE I-continued
ALKYLATION OF BENZENE

Feed: Benzene/Propylene/N$_2$-5/1/5
Contact Time: ~ 3 Seconds
Pressure: 1 Atmosphere

| Example | Catalyst | Temp. (°C.) | Exotherm (°C.) | Catalytic Material (gms) | Selec. (%) | Yield (%) Cumene | Yield (%) Cracked & Rearranged Products* | Productivity (P) | Relative Prod. (PR) $= \frac{\text{P Coated}}{\text{P Uncoated}}$ |
|---|---|---|---|---|---|---|---|---|---|
| 4 | 10% SK-500 90% Alundum (coated) | 302 | 0 | 1.61 | 53.5 | 6.64 | 0 | 1.2145 | 5.199 |
| 5 | 10% SK-500 90% Alundum (coated) | 349 | 1 | 1.61 | 86.4 | 9.94 | Trace | 1.7736 | 12.411 |
| 6 | 10% LZ-Y82 87.5% Alundum 2.5% Silica (coated) | 248 | 1 | 1.70 | 51.8 | 3.22 | 0 | 0.4921 | 1.163 |
| 7 | 10% LZ-Y82 87.5% Alundum 2.5% Silica (coated) | 301 | 3 | 1.70 | 64.8 | 10.18 | 0 | 1.5943 | 2.2714 |
| 8 | 10% LZ-Y82 87.5% Alundum 2.5% Silica (coated) | 352 | 1 | 1.86 | 85.6 | 10.96 | Trace | 1.5686 | 2.2350 |

We claim:

1. A process for producing an alkyl aromatic hydrocarbon comprising contacting an aromatic hydrocarbon with an alkylating agent in the presence of a zeolite catalyst, the improvement comprising using as at least part of the catalyst a coated catalyst having:
   (a) an at least partially porous base support of at least about 20 microns in diameter, said support having an outer surface, and
   (b) a coating substantially on said outer surface, said coating consisting essentially of an active catalytic material containing a zeolite, said coating strongly adhering to said outer surface of said base support.

2. The process of claim 1 wherein the coated catalyst is substantially spherical.

3. The process of claim 2 wherein said substantially spherical catalyst has a diameter of 0.5 mm to 10 mm.

4. The process of claim 3 wherein said substantially spherical catalyst has a diameter of 1 mm to 5 mm.

5. The process of claim 1 wherein the active catalytic material comprises about 1% to 40% by weight of the catalyst particle.

6. The process of claim 5 wherein the active catalytic material comprises about 3% to 12% by weight of the catalyst particle.

7. The process of claim 1 wherein the catalyst charge comprises at least 20% by weight of said coated catalyst.

8. The process of claim 1 wherein the catalyst charge comprises at least 50% by weight of said coated catalyst.

9. The process of claim 1 wherein essentially all of the catalyst charge comprises said coated catalyst.

10. The process of claim 1 wherein ethylbenzene is produced.

11. The process of claim 1 wherein cumene is produced.

12. The process of claim 1 wherein the aromatic hydrocarbon is selected from the group consisting of benzene and naphthalenes.

13. The process of claim 12 wherein the aromatic hydrocarbon is a benzene compound.

14. The process of claim 12 wherein the aromatic hydrocarbon is unsubstituted.

15. The process of claim 12 wherein the aromatic hydrocarbon is substituted with at least one of $C_{1-12}$ alkenes, $C_{6-12}$ cycloalkyls and $C_{6-12}$ aryls.

16. The process of claim 12 wherein the aromatic hydrocarbon is substituted with $C_{1-4}$ alkyls.

17. The process of claim 1 wherein the alkylating agent is selected from the group consisting of:
   (a) $C_{2-10}$ alkenes;
   (b) $C_{1-10}$ alkyl halides;
   (c) $C_{1-10}$ aldehydes; and
   (d) $C_{1-10}$ alcohols; and
   (e) $C_{5-12}$ cyclic olefins.

18. The process of claim 17 wherein the alkylating agent is a $C_{2-4}$ alkene.

19. The process of claim 18 wherein the alkylating agent is at least one of ethylene and propylene.

20. The process of claim 1 wherein the base support is essentially inert.

21. The process of claim 1 wherein the zeolite is selected from the group consisting of:
   (a) X-type zeolites;
   (b) Y-type zeolites;
   (c) mordenite; and
   (d) faujasite.

22. The process of claim 21 wherein the zeolite is a Y-type zeolite.

23. The process of claim 22 wherein the zeolite is a rare earth exchanged Y-type zeolite.

24. The process of claim 1 wherein the zeolite contains less than 1% by weight of sodium or alkali metal.

25. A process for producing an alkylated benzene comprising contacting benzene with a $C_{2-4}$ alkene in the presence of zeolite catalyst, the improvement comprising using as at least part of the catalyst a coated catalyst having:
   (a) an at least partially porous base support of at least about 20 microns in diameter, said support having an outer surface, and
   (b) a coating substantially on said outer surface, said coating consisting essentially of an active catalytic material containing a zeolite, said coating strongly adhering to said outer surface of said base support.

26. A process for producing an alkyl aromatic hydrocarbon comprising contacting an aromatic hydrocarbon with an alkylating agent in the presence of a zeolite catalyst, the improvement comprising using as at least part of the catalyst a coated catalyst prepared by:
 A. Contacting at least a partially porous base support of at least 20 microns in diameter with an excess of liquid in such a manner that the liquid is absorbed by the support to produce a wet support;
 B. Drying the wet support to provide a partially wet support;
 C. Contacting the partially wet support with a powder of an active catalytic material containing a zeolite; and
 D. Gently agitating the mixture of the partially wet support and the active catalyst material containing a zeolite to produce a catalyst which has the active catalytic material strongly adhering as a coating to the outer surface of the base support.

* * * * *